(12) United States Patent
Yoshikawa et al.

(10) Patent No.: US 7,559,224 B2
(45) Date of Patent: Jul. 14, 2009

(54) SENSOR

(75) Inventors: Takaya Yoshikawa, Aichi (JP); Junji Kawai, Aichi (JP); Kenji Hayashi, Gifu (JP); Shinji Tanabe, Aichi (JP); Noboru Ishida, Gifu (JP); Masataka Taguchi, Aichi (JP); Masashi Ando, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 232 days.

(21) Appl. No.: 11/640,215

(22) Filed: Dec. 18, 2006

(65) Prior Publication Data

US 2007/0141911 A1    Jun. 21, 2007

(30) Foreign Application Priority Data

Dec. 19, 2005  (JP)  .............................. 2005-364770
Oct. 18, 2006  (JP)  .............................. 2006-283198

(51) Int. Cl.
*G01N 7/00*    (2006.01)
(52) U.S. Cl. ...................................... 73/23.2
(58) Field of Classification Search .................. 73/23.2
See application file for complete search history.

(56) References Cited

U.S. PATENT DOCUMENTS

| | | | |
|---|---|---|---|
| 5,874,664 A * | 2/1999 | Watanabe et al. | .......... 73/23.32 |
| 6,178,806 B1 * | 1/2001 | Watanabe et al. | .......... 73/23.32 |
| 6,258,234 B1 * | 7/2001 | Watanabe et al. | ........... 204/424 |
| 6,266,997 B1 * | 7/2001 | Nelson | ....................... 73/31.05 |
| 6,360,581 B1 | 3/2002 | Murase et al. | |
| 6,679,099 B2 * | 1/2004 | Fujita et al. | ................... 73/23.2 |
| 6,898,961 B2 * | 5/2005 | Yamada et al. | .............. 73/31.05 |
| 7,467,538 B2 * | 12/2008 | Furuichi et al. | ............... 73/23.2 |
| 2005/0072211 A1 | 4/2005 | Weyl et al. | |
| 2005/0132778 A1 | 6/2005 | Nakagawa | |
| 2007/0167079 A1 * | 7/2007 | Akatsuka et al. | ............ 439/610 |

FOREIGN PATENT DOCUMENTS

JP    11-352095 A    12/1999

* cited by examiner

*Primary Examiner*—Hezron Williams
*Assistant Examiner*—Rodney T Frank
(74) *Attorney, Agent, or Firm*—Sughrue Mion, PLLC

(57) ABSTRACT

A sensor comprising a sensor element, a metallic housing holding therewithin the sensor element, an inner tubular member fixed to an axially rearward end of the metallic housing, and an outer tubular member radially surrounding the inner tubular member and having a radially inward crimping section for contact with an outer surface of the inner tubular member, wherein an axially forward end of the crimping section is disposed axially apart from an axially forward end of the outer tubular member by a distance of 1.5 mm or less.

15 Claims, 10 Drawing Sheets

SENSOR

BACKGROUND OF THE INVENTION

The present invention relates to a sensor and more particularly to a gas sensor such as an oxygen sensor, HC sensor and NOx senor, for detecting a gas component in a gas and a temperature sensor for detecting the temperature of a gas.

It is heretofore known a gas sensor having such a structure in which a sensor element formed at a forward end with a detection portion for detecting a gas component in a gas is disposed inside a metallic casing. The metallic casing is constituted by a plurality of coaxial tubular members such as a metallic housing formed at an outer circumferential surface thereof with a threaded portion for installation of a sensor, a protector connected to the metallic housing in such a manner as to cover the detection portion of the sensor element, which protrudes from the forward end of the metallic housing, an inner tubular member connected to a rearward open end portion of the metallic housing and covering a portion of the sensor element, which extends rearward from the rearward open end portion, and an outer tubular member radially surrounding an outer circumferential periphery of the inner tubular member while interposing therebetween a water repellant filter.

Such a gas sensor (e.g., oxygen sensor) is installed on, for example, an exhaust pipe of an exhaust system of an automotive engine or the like. Further, it is recently a general practice to provide the exhaust pipe with a catalytic device for decomposing a toxic substance in an exhaust gas and dispose a gas sensor downstream of the catalytic device thereby measuring a detection component in an exhaust gas from which a toxic substance has been removed. In this instance, since the gas sensor is disposed downstream of the exhaust pipe that extends rearward from the engine and along the bottom of a vehicle body, water drops or the like may adhere to the outer surface of the gas sensor. Accordingly, in order to prevent the water drops or the like from entering into the gas sensor, it is important for the plurality of tubular members to be joined assuredly together for attaining the water tightness of the gas sensor.

Crimping is known as a method of joining the plurality of tubular bodies together. For example, it is known a gas sensor in which a protector is fixed to a forward end of a metallic housing by crimping, a forward end of an inner tubular member is fixed to a rearward end of the metallic housing by crimping, a forward overlying portion of the outer tubular member, which overlies on the inner tubular member, is fixed to the inner tubular member by crimping as disclosed in Unexamined Japanese Patent Publication No. 11-352095. In this sensor, the outer tubular member is formed at the forward side with a crimping section (crimped fixing section) in the form of an annular recess extending circumferentially there around, i.e., decreased in diameter so as to allow the forward end of the crimping section to fittingly engage the outer surface of the inner tubular member, thereby closing a space between the inner tubular member and the outer tubular member. Accordingly, by forming such crimping sections at predetermined places, a single-piece tubular body having a high water tightness can be obtained.

SUMMARY OF THE INVENTION

In the meantime, in order to allow movement of the crimping position at the forward side of the outer tubular member within the error range, the crimping position is arranged in many cases at the place a little apart rearward from the forward end of the outer tubular member. However, if the crimping is carried out at that place, the remaining portion of the outer tubular member, which is positioned more forward than the crimping section, is caused to float a little above the outer surface of the inner tubular member, so that a little space or gap is formed between the forward end of the outer tubular member and the outer surface of the inner tubular member. Then, water drops adhered to the outer surface of the gas sensor are introduced by capillary action into the gap and held therein for a long period of time due to the surface tension of the water.

Particularly, in case aqueous solution containing metallic salt, such as salt water (water containing salt) is drawn into the gap, a chemical reaction may possibly occur between the inner surface of the outer tubular member and the outer surface of the inner tubular member to cause both of the outer surface of the inner tubular member and the inner surface of the outer tubular member to rust. For example, in cold, snowy terrains, it is a general practice to scatter a snow-melting agent containing calcium chloride as a major constituent, so that puddles or pools are caused by melted snow on the ground and contain salt water that is produced by dissolution of calcium chloride. Accordingly, when automotive vehicles are caused to pass over the pools, salt is adhered onto the surface of the gas sensor. Then, salt water is drawn into the gap between the forward end of the outer tubular member and the outer circumferential surface of the inner tubular member and held there within, so that there have been a possibility of the inner tubular member and the outer tubular member being caused to rust. Further, the progress of rusting may cause a crack or cracks in the inner tubular member, thus possibly allowing salt water to go into the outer tubular member through the crack or cracks and lowering the detection accuracy of the sensor.

Further, the outer tubular member, when crimped, gets a similar effect to that a sheet of metal gets when forcedly bent, so that when the pressure is removed immediately after crimping the crimped outer tubular member causes a spring back phenomenon due to reaction thereof. If the crimping section is formed at the place that is spaced apart rearward from the forward end of the outer tubular member, the spring back phenomenon is enhanced or increased. Accordingly, immediately after the outer tubular member is crimped, the forward end of the crimping section is pulled by the above-described remaining portion of the outer tubular member, thus causing a possibility of the entire crimping section being curved a little radially outward. For this reason, it is supposed that the surface pressure of the inner tubular member at the crimping section relative to the outer surface of the inner tubular member is a little lowered. This may possibly leads to decrease in the fitness in engagement of the crimping section with the outer surface of the inner tubular member and therefore is causative of decreasing the water tightness of the gas sensor.

It is accordingly an object of the present invention to provide a sensor or gas sensor that is free from the above-noted problems in the prior art devices and that is capable of preventing rusting of the outer tubular member and the inner tubular member due to salt water adhered thereto and improving the water tightness.

To achieve the above object, the present provides a sensor comprising a sensor element, a metallic housing holding there within the sensor element, an inner tubular member fixed coaxially to an axially rearward end of the metallic housing, and an outer tubular member radially and coaxially surrounding the inner tubular member and having a radially inward crimping section for contact with an outer surface of the inner tubular member, wherein an axially forward end of the crimping section is disposed axially apart from an axially forward end of the outer tubular member by a distance of 1.5 mm or less.

DESCRIPTION OF THE PREFERRED EMBODIMENTS

Figure 1:
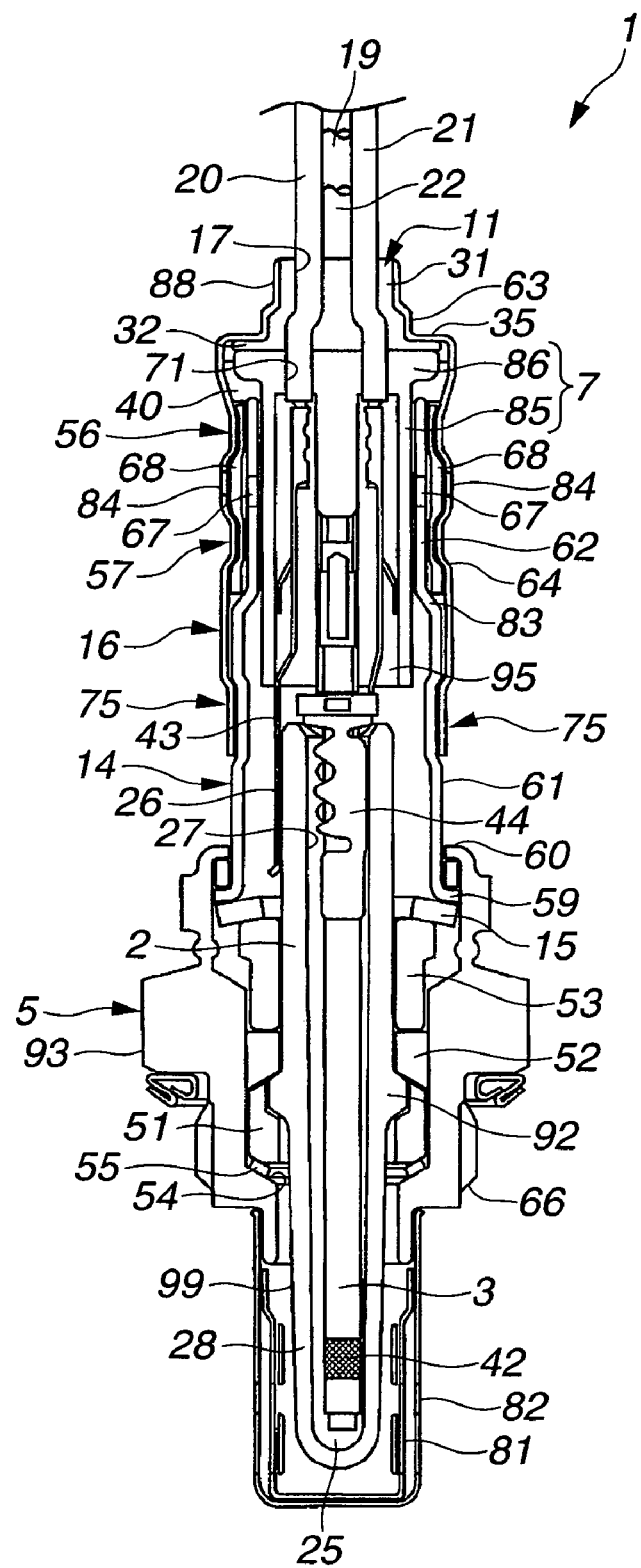
FIG. 1 is a sectional view of a gas sensor according to a first embodiment of the present invention.

Referring first to FIG. 1, a gas sensor 1 according to a first embodiment of the present invention is of the kind installed on an exhaust pipe of an automotive vehicle for detecting an oxygen concentration in an exhaust gas flowing through the exhaust pipe.

Firstly, the gas sensor 1 will be described. As shown in FIG. 1, the gas sensor 1 includes a sensor element 2 that is closed at a forward end so as to have a bottomed tubular shape, a ceramic heater 3 inserted into a bottomed hole of the sensor element 2, a metallic housing 5 for holding there within the sensor element 2, an inner tubular member 14 connected to a rearward end of the metallic housing 14, and an outer tubular member disposed coaxially with the inner tubular member and having a rearward side of the inner tubular member inserted there into. In the meantime, of the axial directions of the sensor element 2 shown in FIG. 1, the direction toward a leading end portion that is exposed to a measurement gas (exhaust gas), i.e., the direction toward the closed end side or the lower side in the drawing, is referred to as "forward" and the direction opposite thereto, i.e., the direction toward the upper side in the drawing is referred to as "rearward".

Then, the sensor element 2 will be described. The sensor element 2 has at an axially forward side thereof a detection portion (no numeral) at which the sensor element 2 detects a gas component in a measurement gas. Specifically, the sensor element 2 includes an oxygen ion conductive solid electrolyte 28 containing yttria partially stabilized zirconia as the major constituent, an inner electrode layer 27 formed on the inner surface of the bottomed hole 25 of the solid electrolyte 28 so as to cover nearly the entire surface and formed of Pt or Pt alloy so as to constitute a porous electrode, and an outer electrode 26 formed on the outer surface of the solid electrolyte 28 so as to constitute a porous electrode similarly to the inner electrode 27. Further, the sensor element 2 is provided with a porous electrode protection layer 99 coating the outer electrode layer 26 and formed of heat-resistant ceramic such as a porous alumina-magnesia spinel. Further, at the axially nearly intermediate position of the sensor element 2 is provided a flange portion 92 that protrudes radially outward. Further, the ceramic heater 3 is rod-shaped and provided with a heating portion 42 having a heating resistor at the inside thereof. When the ceramic heater 3 is energized by way of heater lead wires 19 and 22 which will be described later, the heating portion 42 heats thereby performing a function of heating the sensor element 2 with a view to activating the sensor element 2.

Then, the metallic housing 5 will be described. The metallic housing 5 has an externally threaded portion 66 for attaching the gas sensor 1 to an attaching portion of an exhaust gas and a hexagonal portion 93 with which a tool is coupled or engaged at the time of attachment of the gas sensor 1 to the attaching portion of the exhaust pipe.

Then, at a forward inner circumferential periphery of the metallic housing 5 is provided a shoulder portion 54 that protrudes radially inward. Upon the shoulder portion 54 is fixedly supported a support member 51 made of alumina by way of a packing 55. In the meantime, the sensor element 2 is held by the metallic housing 5 by being supported at the flange portion 51 upon the support member 51. Between an inner surface portion of the metallic housing 5, which is positioned at the rearward side of the support member 51, and the outer surface of the sensor element 2 is filled a filling member 52 formed of talc powder. At the rearward side of the filling member 52 are disposed in sequence a sleeve 53 made of alumina and a circular ring 15 in a way as to be inserted into the metallic housing 5 coaxially.

Further, to the forward end outer circumferential periphery of the metallic housing 5 are attached dual protectors 81 and 82 made of metal. The dual protectors 81 and 82 have a plurality of gas inlet holes and are adapted to cover the detection portion of the sensor element 2 which protrudes from the forward end of the metallic housing 5.

Then, the inner tubular member 14 will be described. The inner tubular member 14 is made of SUS304L according to JIS G3549 and has a forward end inserted into the rearward end of the metallic housing 5. Then, the inner tubular member 14 is fixedly attached to the metallic housing 5 by crimping a rearward end 60 of the metallic housing 5 against the inner tubular member 14 under the condition where an increased-diameter forward end 5 is abuttingly engaged with an annular ring 15. In the meantime, the gas sensor 1 is structured so that crimping of the rearward end portion 60 of the metallic housing 5 causes the filling member 53 to be compressed and filled by way of the sleeve 53. By this, the sensor element 2 is held in a watertight manner within the metallic housing 5.

Further, the inner tubular member 14 is formed with a shoulder portion 83 at the axially nearly intermediate position thereof, the side more forward than the shoulder portion 83 being formed as a forward portion 61 and the side more rearward than the shoulder portion 83 being formed as a rearward portion 62. The rearward portion 62 is smaller both in the inner diameter and the outer diameter than the forward portion 61, and its inner diameter is a little larger than the outer diameter of a main body portion 85 of a separator 7 which will be described later. Further, the rearward portion 62 is formed with a plurality of air inlet holes 67 arranged circumferentially at predetermined intervals.

Then, the outer tubular member 16 will be described. The outer tubular member 16 is formed from a sheet of SUS304L according to JIS G3549 into a tubular shape and includes a rearward portion 63 having an opening providing communication between the outside and the inside, a forward portion 64 connected, at a forward side thereof, coaxially with the rearward side of the inner tubular member 14 and a shoulder portion 35 connecting between the rearward portion 63 and the forward portion 64. In the meantime, the rearward portion 63 is formed with a crimping section 88 for water tightly and fixedly holding elastic seal member 11.

Further, at the outside of the rearward portion 62 of the inner tubular member 14 is disposed a tubular filter 68 for preventing the entrance of water from the air inlet holes 67. In the meantime, the filter 68 is constructed as a water repellent filter that prevents the passage of liquid mainly consisting of water while on the other hand allowing the passage of gas such as air, like a porous, fiberous structure of polytetrafuluoroethylene (sold under the name of Gore-Tex by Japan Gore-Tex, Inc.) for instance.

Further, the forward portion 64 of the outer tubular member 16 is so shaped as to surround the inner tubular member 14 (specifically, the rearward portion 62) having the filter 68 disposed thereon, and formed with, at a position corresponding to the filter 68, a plurality of air inlet holes 84 arranged circumferentially at predetermined intervals.

Then, the connection between the inner tubular member 14 and the outer tubular member 16 will be described. As shown in FIG. 1, the outer tubular member 16 and the inner tubular member 14 are fixed by a first crimping section 56 which is formed by crimping radially inward, by way of the filter 68, at least a portion of the forward portion 64 of the outer tubular member 16, which is positioned more rearward than the air inlet holes 84 and by crimping radially inward, similarly by way of the filter 68, at least a portion of the outer tubular forward portion 64, which is positioned more forward than the air inlet holes 84. At this time, the filter 68 is held in a watertight state between the outer tubular member 16 and the inner tubular member 14. Further, the forward portion 64 of the outer tubular member 16 is disposed so as to lie over the forward portion 61 of the inner tubular member 14. Further, by crimping a part of an overlying portion of the outer tubular member 16 radially inward against the inner tubular member 14, a crimping section 75 that is reduced in diameter is formed. In the meantime, in this embodiment, the crimping section 75 is adjusted so as to be positioned at the forward end of the above-described overlying portion. In this connection, an important feature of the present invention resides in the position at which the crimping section 75 is formed, and its operation and effect will be described later.

In this manner, by fixing the outer tubular member 16 to the inner tubular member 14 by crimping, the both are fittingly joined together without any looseness. The air that serves as a reference gas is introduced through air introducing holes 84, the filter 68 and air inlet holes 67 into the bottomed hole 25 of the sensor element 2. On the other hand, a water drop is prevented from entering into the inside of the inner tubular member 14 since it cannot pass the filter 68.

Then, description will be made as to the inside structure of the inner tubular member 14 and the outer tubular member 16. As shown in FIG. 1, at the inside of the rearward portion 62 of the inner tubular member 14 is disposed the above-described separator 7 which is hollow, nearly cylindrical. The separator 7 is formed with lead wire insertion holes 71 which penetrate between the forward end and the rearward end thereof and into which sensor element lead wires 20, 21 and heater lead wires 19, 22 are inserted to pass there through. Further, the separator 7 is formed with a bottomed retaining hole 95 that opens at the forward end surface thereof. Into the retaining hole 95 is inserted a rearward portion of the ceramic heater 3, and by abutting engagement of a rearward end surface of the ceramic heater 3 with a bottom surface of the retaining hole 95, the axial position of the ceramic heater 3 relative to the separator 7 is determined.

Further, the separator 7 has a main body portion 85 that is inserted into the rearward inside of the inner tubular member 14 and a flange portion 86 that extends radially outward from the rearward end of the main body portion 85. Namely, the separator 7 is disposed inside the outer tubular member 16, with the main body portion 85 being inserted into the inner tubular member 14 and the flange portion 86 being supported on the rearward end surface of the inner tubular member 14 by way of an annular seal member 40 made of fluororubber.

On the other hand, at the rearward side of the separator 7 is disposed the elastic seal member 11 made of fluororubber or the like that has an excellent heat resisting ability. This elastic seal member 11 has a main body portion 31 and a flange portion 32 that extends radially outward from a forward end of the main body portion 31. Further, the elastic seal member 11 is formed with four lead wire insertion holes 17 that extend axially through the main body portion 31. The elastic seal member 11 is inserted into the rearward inside of the outer tubular member 16 and is fixed to the outer tubular member 16 by the crimping section 88 of the outer tubular member 16.

Further, the sensor element lead wires 20, 21 and the heater lead wires 19, 22 are disposed so as to extend through the lead wire insertion holes 71 of the separator 7 and the lead wire insertion holes 17 of the elastic seal member 11 and then allowed to get out from the inside of the inner tubular member 14 and the outer tubular member 16 to the outside. In the meantime, these four lead wires 19, 20, 21 and 22 are connected at the outside to connectors (not shown). Through the connectors is performed transmission of electrical signals between external devices such as ECU and the respective lead wires 19, 20, 21 and 22.

Further, each of the lead wires 19, 20, 21 and 22, though not shown in detail, is constructed so as to cover a conductor by an insulating layer made of resin and connected at the rearward end of the conductive wire to a connector terminal provided to a connector. The forward end of the conductor of the sensor lead wire 20 is joined together by crimping with the rearward end of a metallic terminal member 43 that is fitted on the outer surface of the sensor element 2. The forward end of the sensor lead wire 21 is joined together by crimping with the rearward end of a metallic terminal member 44 that is press-fitted in the inner circumferential periphery of the sensor element 2 and is electrically connected to the inner electrode layer 27. On the other hand, the heater lead wires 19, 22 are connected with respective heater metallic terminal members which are in turn connected to heating resistors of the ceramic heater 3.

Then, the position at which the crimping section 75 is formed, which is an important feature of the present invention, will be described. In the gas sensor 1 of this embodiment, the crimping section 75 is adjusted so as to be positioned at the most forward side of the overlapped section of the forward portion 64 of the outer tubular member and the forward portion 61 of the inner tubular member 14. By this, the forward end 64a of the outer tubular member 16 is crimped against the outer surface of the forward portion 61 of the inner tubular member 14, thus enabling the forward end 64a of the outer tubular member 16 to fittingly engage or contact the outer surface of the forward portion 61 of the inner tubular member 14. Thus, a gap or space 90 (refer to FIGS. 3 and 4) is not formed between the inner surface of the forward end 64a portion of the outer tubular member 16 and the outer surface of the forward portion 61 of the inner tubular member 14, and therefore salt water is not stored therebetween. Further, since salt water is not stored, there is no possibility of the forward portion 61 of the inner tubular member 14 and the forward portion 64 of the outer tubular member 16 being corroded.

Further, the outer tubular member 16 is 0.8 mm thick and the inner tubular member 14 is 1.6 mm thick. In this manner, by making the outer tubular member 16 be thinner than the inner tubular member 14, it becomes possible to further reduce the spring back phenomenon caused at the crimping section 75. As a result, the outer tubular member 16 can engage or contact at the crimping section 75 with the outer surface of the inner tubular member 14 with improved fitness. Further, in case the thickness of the outer tubular member 16 is in the range from 0.3 to 0.8 mm, it becomes possible to effectively prevent the surface pressure against the inner tubular member at the crimping section 75 from being lowered.

Further, the Vickers hardness (HV) of the outer tubular member 16 at the crimping section 75 is 140 and the Vickers hardness (HV) of the inner tubular member 14 at the crimping section 75 is 370. In this manner, by constructing the gas sensor 1 so that the Vickers hardness of the outer tubular 16 at the crimping section 75 is lower than that of the inner tubular member 14 at the crimping section 75, the spring back phenomenon caused at the crimping section 75 can be reduced further and the fitness with which the outer tubular member 16 is fittingly engaged at the crimping section 75 with the outer surface of the inner tubular member 14 can be improved. Further, by using austenite stainless steel for the outer tubular member 16, reduction in the surface pressure against the inner tubular member 14 at the crimping section 75 can be effectively prevented.

Then, in order to recognize a variation in the effect depending upon a variation in the forming position of the crimping section 75, the following two evaluation tests were conducted. By the first evaluation test, it was evaluated a variation in the shape of the forward portion 64 of the outer tubular member 16 depending upon a variation in the forming position of the crimping section 75. By the second evaluation test, it was analyzed by the FEM analysis a variation in the surface pressure against the forward portion 61 of the inner tubular member 14 at the crimping section 75 depending upon a variation in the forming position of the crimping section 75.

Firstly, the first evaluation test will be described. In the first evaluation test, a plurality of examples of the gas sensor 1 before crimping of the forward portion 64 of the outer tubular member 16 were prepared. The crimping work of the forward portion 64 of each example was performed in such a manner that the examples differ in the forming position of the crimping section 75 from each other but the forming positions were included in the overlying part of the forward portion 64 of the outer tubular member 16 and the forward portion 61 of the inner tubular member 14. Then, it was evaluated that the forward end shape of the forward portion 64 of the outer tubular member 16 at the overlying part of each of the examples. In the meantime, in the description that will be made hereinafter, the position of the forward end of the crimping section 75 is referred to as a crimp forward end position P. By adjusting variously the distance by which the crimp forward end position P and the forward end 64a of the forward portion 64 of the outer tubular member 16 are placed apart from each other, the forming position of the crimping section 75 was adjusted.

Figure 2:
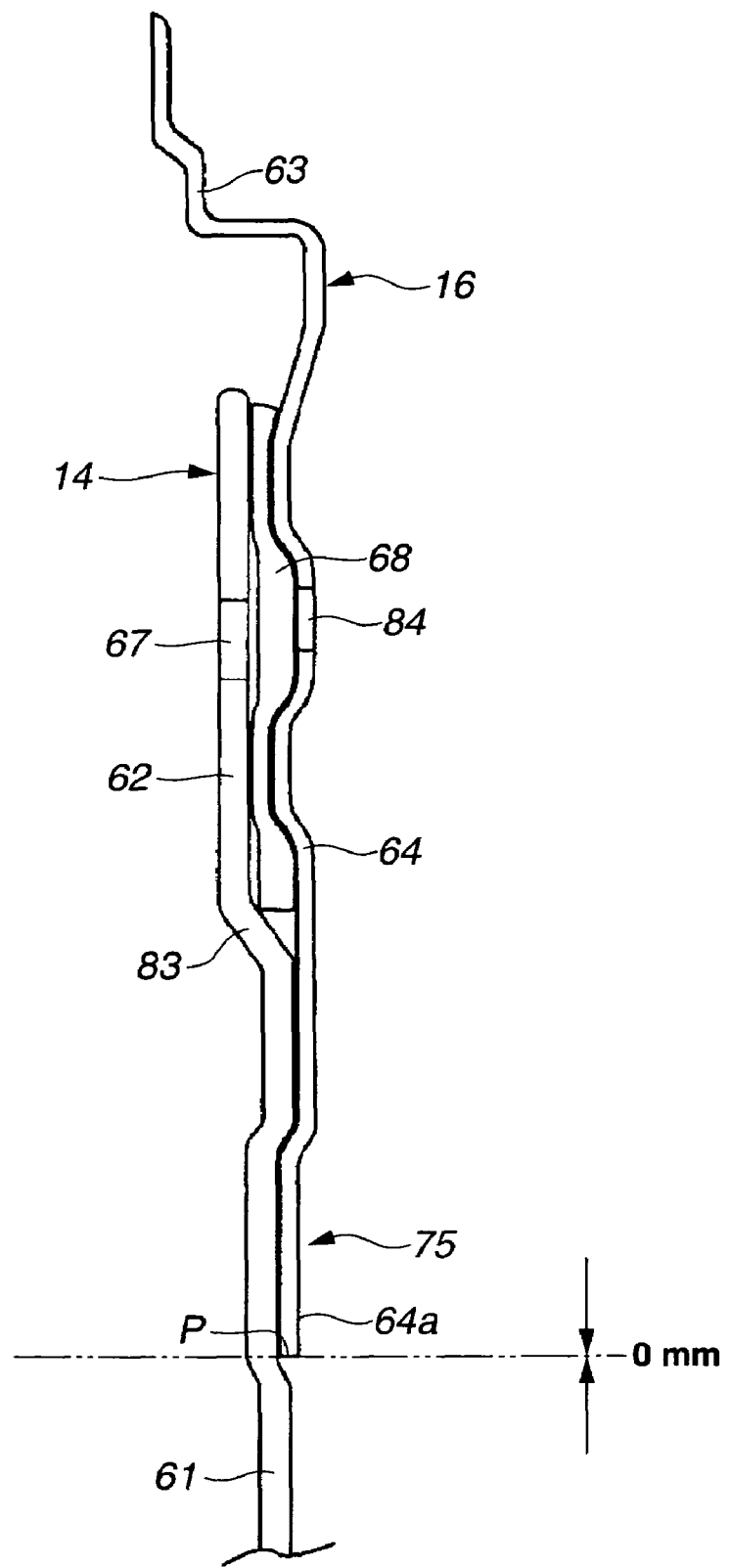
FIG. 2 is an enlarged sectional view of a crimping section and its adjacent portion of an outer tubular member of the gas sensor of FIG. 1 (axial distance between crimp forward end position P and forward end of outer tubular member is 0 mm)
Figure 3:
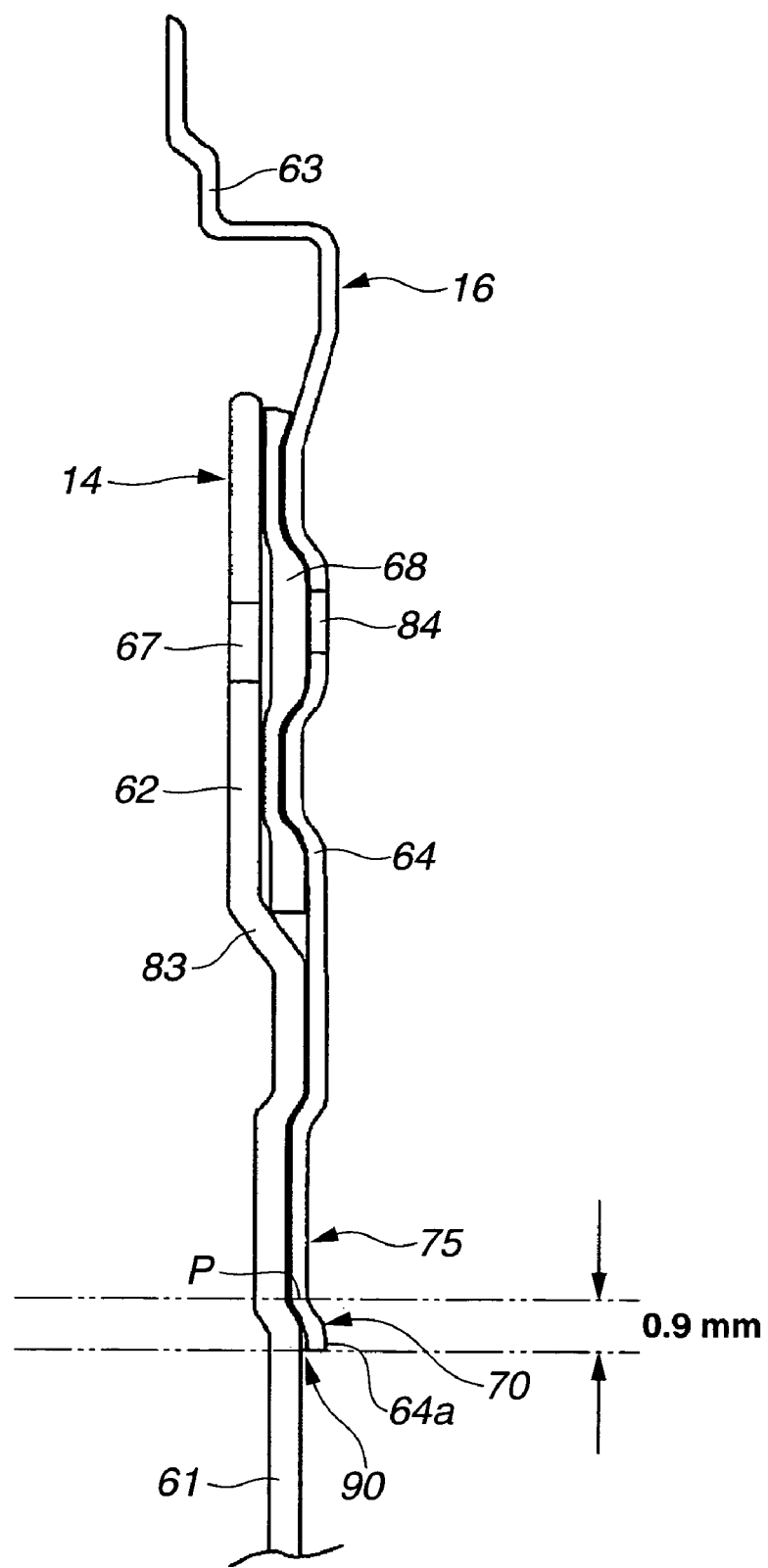
FIG. 3 is an enlarged sectional view of a crimping section and its adjacent portion of an outer tubular member of the gas sensor of FIG. 1 (axial distance between crimp forward end position P and forward end of outer tubular member is 0.9 mm)

Then, the shape of the forward portion 64 of the outer tubular member 16 at the overlying part of each example will be described. For example, in case as shown in FIG. 2, the distance between the crimp forward end position P and the forward end 64a of the outer tubular member 16 is 0 (zero) mm, a skirt section 70 (refer to FIG. 3) which will be described in later is not formed. On the other hand, in case as shown in FIG. 3, the distance between the crimp forward end position P and the forward end 64a of the outer tubular member 16 is 0.9 mm, the skirt section 70 is formed at the forward side of the forward portion 64 of the outer tubular member 16, in which the forward end 64a is caused to flare a little. The axial length of the skirt section 70 is equal to the distance between the crimp forward end position P and the forward end 64a of the outer tubular member 16, i.e., 0.9 mm. Further, inside the skirt section 70 is formed a space or gap 90 of a nearly ring-shaped cross section.

Figure 4:
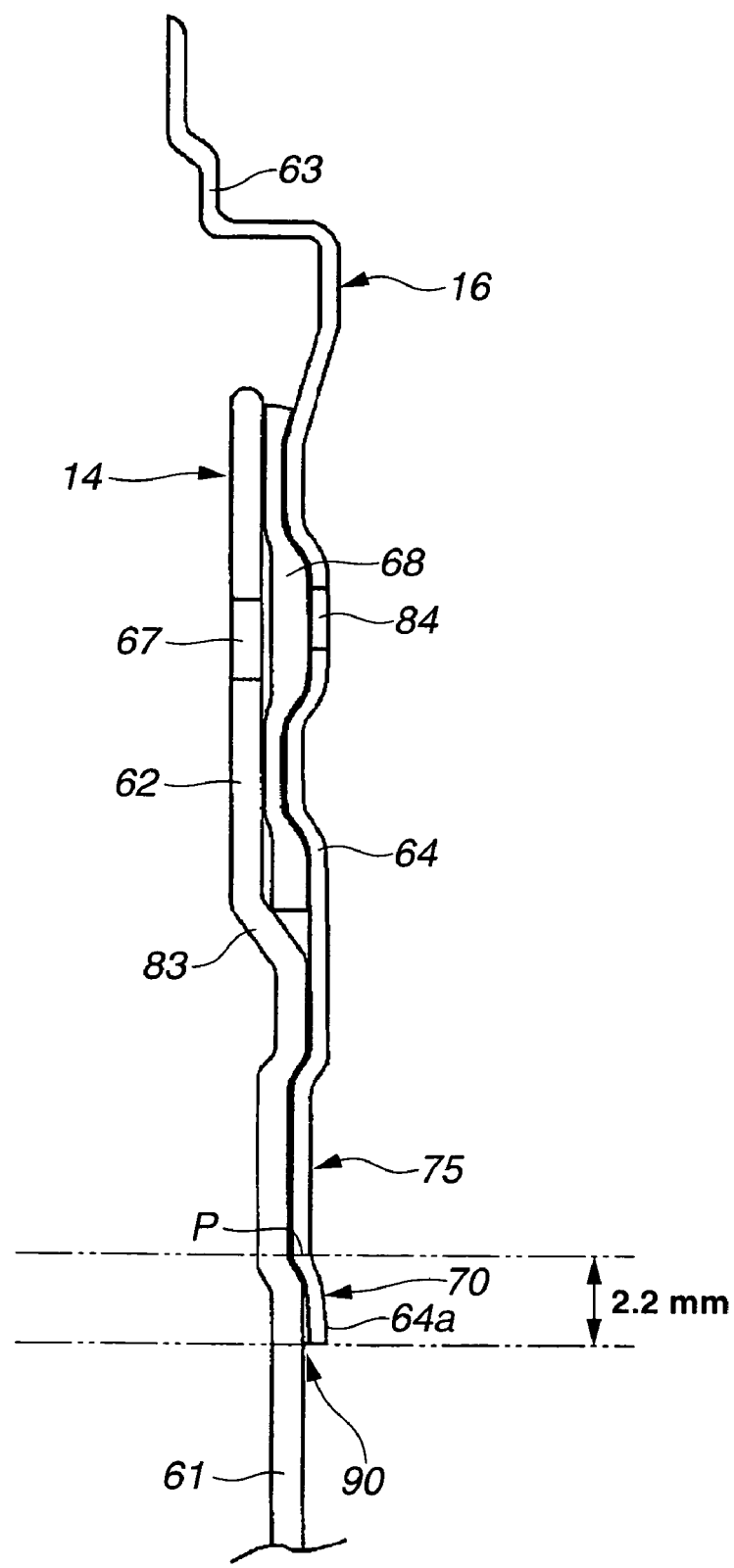
FIG. 4 is an enlarged sectional view of a crimping section and its adjacent portion of an outer tubular member of the gas sensor of FIG. 1 (axial distance between crimp forward end position P and forward end of outer tubular member is 2.2 mm)
Figure 5:
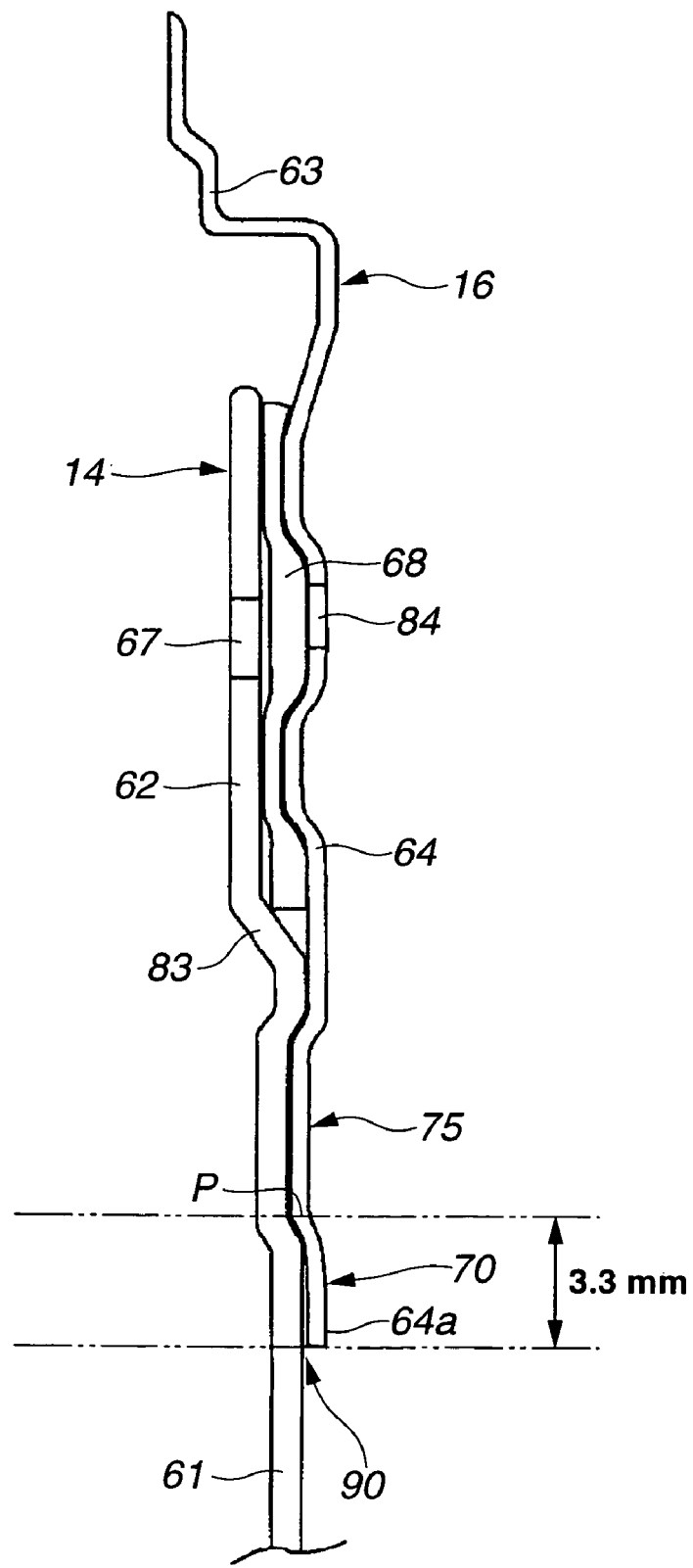
FIG. 5 is an enlarged sectional view of a crimping section and its adjacent portion of an outer tubular member of the gas sensor of FIG. 1 (axial distance between crimp forward end position P and forward end of outer tubular member is 3.3 mm)
Figure 6:
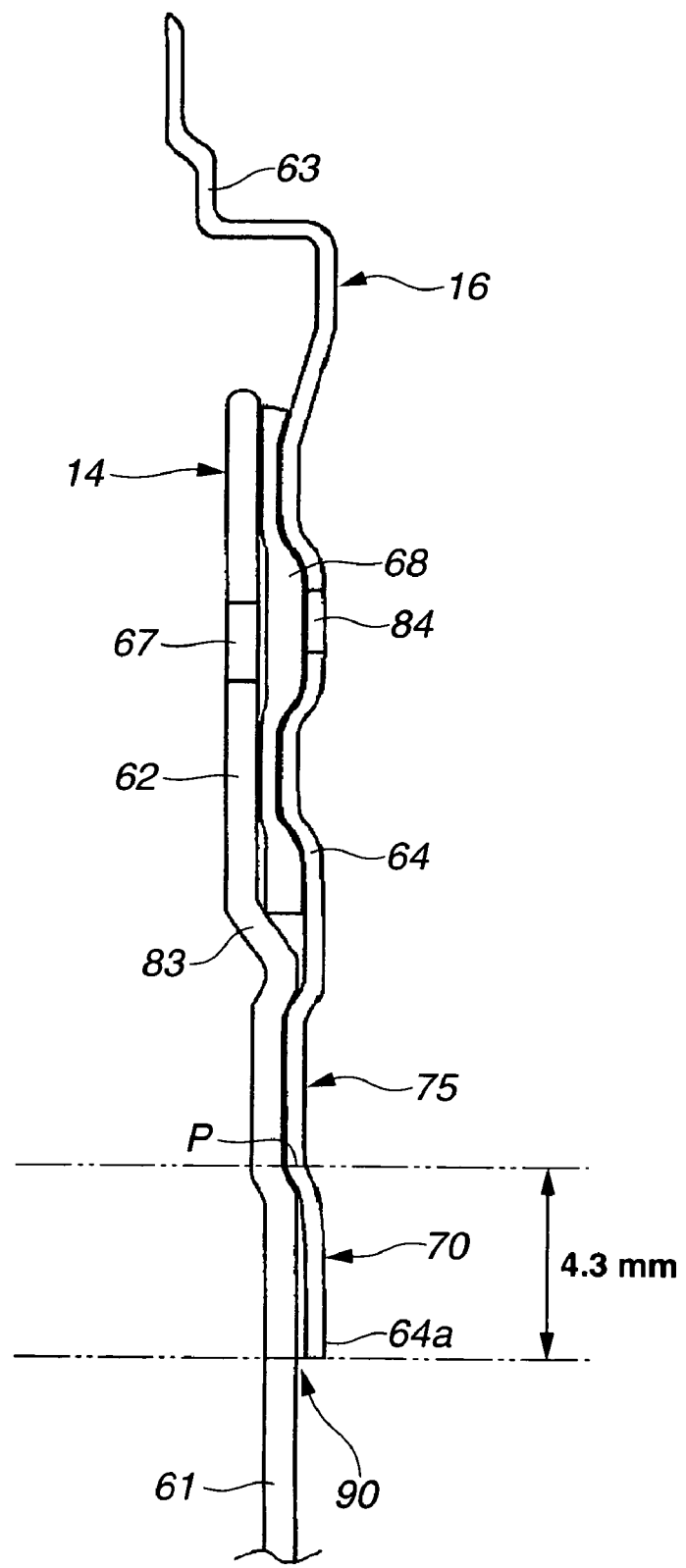
FIG. 6 is an enlarged sectional view of a crimping section and its adjacent portion of an outer tubular member of the gas sensor of FIG. 1 (axial distance between crimp forward end position P and forward end of outer tubular member is 4.3 mm)

Further, as shown in FIGS. 4 and 5, in case the forming position of the crimping section 75 is moved axially rearward in such a manner that the distance between the crimp forward end position P and the forward end 64a of the outer tubular member 16 is 2.2 mm or 3.3 mm, the axial length of the skirt section 70 is increased to be 2.2 mm or 3.3 mm. In response to this, the axial length of the gap 90 is increased. Then, as shown in FIG. 6, the forming position of the crimping section 75 is moved so as to be placed at the most rearward section or the section adjacent thereto of the overlying part of the forward portion 64 of the outer tubular member 16 and the forward portion 61 of the inner tubular member 14 in such a manner that the distance between the crimp forward end position P and the forward end 64a of the outer tubular member 16 is 4.3 mm, the length of the skirt section 70 is increased further to be 4.3 mm. In response to this, the axial length of the gap 90 is increased further.

In this manner, as the forming position of the crimping section 75 is moved axially rearward, the axial length of the skirt section 70 formed at the forward side of the forward portion 64 of the outer tubular member 16 is increased. Further, when the skirt section 70 is increased in the axial length, the gap 90 is increased in the axial length so that the amount of salt water stored in the gap 90 is increased. In this instance, since a chemical reaction is liable to be caused between the outer surface of the forward portion 61 of the inner tubular member 14 and the inner surface of the forward portion 64 of the outer tubular member 16, it is supposed that there is caused a high possibility of the forward portion 61 of the inner tubular member 14 and the forward portion 64 of the outer tubular member 16 being corroded. Accordingly, as in this embodiment, by adjusting so that the forming position of the crimping section 75 is placed at the most forward side of the overlying part of the forward portion 64 of the outer tubular member 16 and the forward portion 61 of the inner tubular member 14, the skirt section 70 otherwise formed at the forward side of the forward portion 64 of the outer tubular member 16 can be eliminated as shown in FIG. 2 or can be made smaller, while at the same time the gap 90 can be eliminated or made smaller, thus making it possible to prevent corrosion of the forward portion 61 of the inner tubular member 14 and the forward portion 64 of the outer tubular member 16.

Then, the second evaluation test will be described. In the second evaluation test, in case the forming position of the crimping section 75 is varied in the range of the overlying part of the forward portion 64 of the outer tubular member 16 and the forward portion 61 of the inner tubular member 14, the surface pressure applied from the crimping section 75 against the outer surface of the forward portion 61 of the inner tubular member 14 is evaluated by the FEM analysis.

Herein, the FEM analysis will be described. First, SUS430 is used for both of the inner tubular member 14 and the outer tubular member 16. The forward portion 61 of the inner tubular member 14 and the forward portion 64 of the outer tubular member 16 before crimping are shaped so that the forward portion 61 of the inner tubular member 14 is 13.8 mm in outer diameter and 12.2 mm in inner diameter and the forward portion 64 of the outer tubular member 16 is 15.1 mm in outer diameter and 14.3 mm in inner diameter. Further, after crimping, the outer diameter of the forward portion 64 of the outer tubular member 16 is 13.65 mm. Namely, it is calculated the surface pressure against the outer surface of the forward portion 61 of the inner tubular member 14 at the crimping section 75 when the crimping is performed until the forward portion 64 of the outer tubular member 16 is reduced to 13.65 mm. Further, the number of examples for the evaluation is eleven in total, in which examples the axial lengths of the skirt sections 70 are varied from 0 to 5.2 mm, respectively. On the basis of the analysis condition, the relation between the axial length of the skirt section 70 and the surface pressure in each of the examples was obtained.

Figure 7:
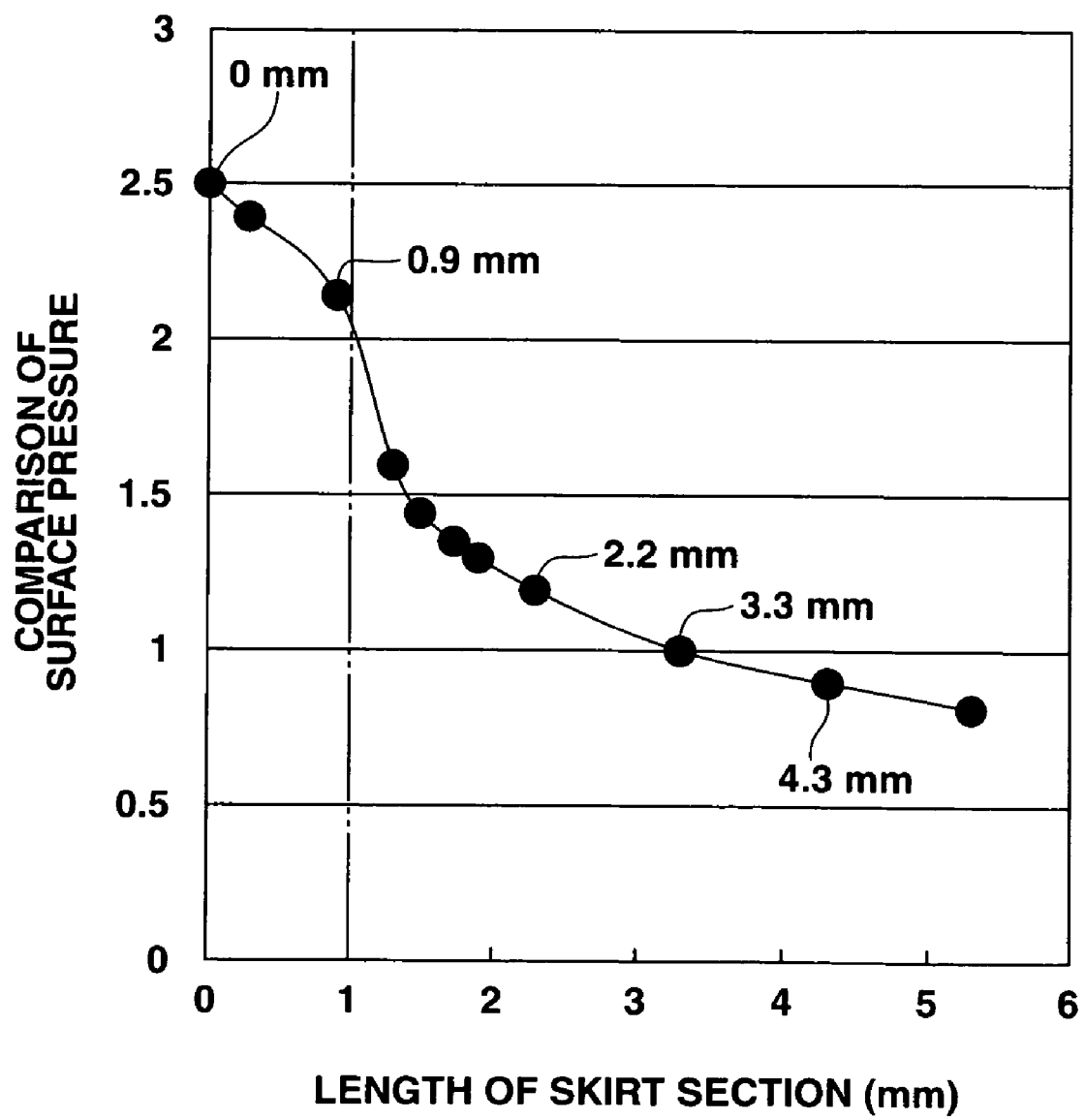
FIG. 7 is a graph showing the result of an FEM (Finite Element Method) analysis.

Then, the result of the FEM analysis will be described. In the meantime, the surface pressure relative to the axial length of the skirt section 70 is represented by the ratio when the surface pressure obtained by calculation in case the axial length of the skirt section is 3.3 mm is determined as 1 (one). As shown in FIG. 7, in case, for example, the ratio is 2.5 when the length of the skirt section 70 is 0 mm (refer to FIG. 2), 2.2 when 0.9 mm (refer to FIG. 2), 1.3 when 2.2 mm (refer to FIG. 4, and 0.9 when 4.3 mm (refer to FIG. 6), i.e., the ratio is generally represented by an S-like curve that descends as it goes rightward. The surface pressure is lowered sharply when the axial length of the skirt section 70 exceeds 1 mm, changes in a way as to be presented by curved lines when the axial length of the skirt section 70 is 1.3 mm and 1.5 mm, and has a tendency to decrease gradually when the axial length of the skirt section 70 exceeds 3 mm.

In the meantime, it is considered that the surface pressure is lowered for the following reason. The forward portion 64 of the outer tubular member 16, when crimped, receives the same effect as a sheet of metal that is forcedly bent. By this, when the pressure is released immediately after crimping, there is caused in the forward portion 64 of the outer tubular member 16 a spring back phenomenon, i.e., the crimping section 75 springs back being pulled by the skirt section 70. Accordingly, the crimping section 70 expands radially outward a little in its entirety, and it is supposed that for such reason, the surface pressure applied by the crimping section 75 against the outer surface of the forward portion 61 of the inner tubular member 14 is lowered. From the result of the above-described analysis, it is revealed that the more the surface pressure at the crimping section 75 decreases, the more the axial length of the skirt section 70 increases, and therefore it is assumed that the fitness in contact between the crimping section 75 and the outer surface of the forward portion 61 can be improved when the forming position of the crimping section 75 is adjusted so that the axial length of the skirt section 70 is 1.5 mm or less (preferably 1.3 mm or more preferably 1.0 mm).

As having been described, in the gas sensor of this embodiment, the forming position of the crimping section 75 is adjusted so as to be located at the most forward side of the overlying part of the forward portion 64 of the outer tubular member 16 and the forward portion 61 of the inner tubular member 14. More specifically, the crimp forward end position P that is the forward end of the crimping section 75 and the forward end 64*a* of the outer tubular member 16 are adjusted so as be disposed at the same position (i.e., the distance therebetween is 0 mm). By this, the forward end 64*a* of the outer tubular member 16 is crimped against the outer surface of the forward portion 61 of the inner tubular member 14 such that the forward and 64*a* of the outer tubular member 16 can be fittingly engaged with the outer surface of the forward portion 61 of the inner tubular member 14. Further, since there is not formed any space between the inner surface of the forward end 64*a* of the outer tubular member 16 and the outer surface of the forward portion 61 of the inner tubular member 14, salt water is not stored at any place and therefore the inner tubular member 14 and the outer tubular member 16 has no possibility of being corroded.

Further, in case the forming position of the crimping section 75 is moved rearwardly away from the forward end 46*a* of the outer tubular member 16, the skirt section 70 is formed at the forward end of the forward portion 64 of the outer tubular member 16. This skirt section 70 is causative of the spring back phenomenon at the forward portion 64 of the outer tubular member 16. However, by forming the crimping section 75 at the most forward side of the overlying part of the forward portion 64 of the outer tubular member 16 and the forward portion 61 of the inner tubular member 14 in this embodiment, such a skirt section 70 is not formed. By this, the spring back phenomenon can be avoided, and it becomes possible to prevent the fitness in contact between the crimping section 75 and the forward portion 61 of the inner tubular member 14 from being lowered.

In the meantime, the sensor and the gas sensor of this invention are not limited to the above-described embodiment but various modification and variations thereof are possible. Namely while in the above-described embodiment, the skirt section 70 otherwise formed at the forward side of the forward portion 64 of the outer tubular member 16 is eliminated by forming the crimping section 75 at the most forward side of the overlying part of the forward portion 64 of the outer tubular member 16 and the forward portion 61 of the inner tubular member 14, it will suffice that the distance between the forward end 64*a* of the outer tubular member 16 and the crimp forward end position P that indicates the forward end of the crimping section 75 is at least 1.5 mm or less.

Further, while the above-described embodiment is adapted not to form the skirt section 70 by disposing the forming position of the crimping section 75 at the most forward side of the overlying part of the forward portion 64 of the outer tubular member 16 and the forward portion 61 of the inner tubular member 14, it will suffice that, for example, the skirt section 70 may be cut off after the crimping section 75 is formed.

Further, in this embodiment, there is no particular limitation about the width of crimp of the crimping section 75.

Further, while in the above-described embodiment the outer tubular member 16 and the inner tubular member 14 are fixed by the crimping section 75, this is not for the purpose of limitation but the axially central portion of the crimping section 75 may be processed by laser welding after the crimping section 75 is formed.

Figure 8:
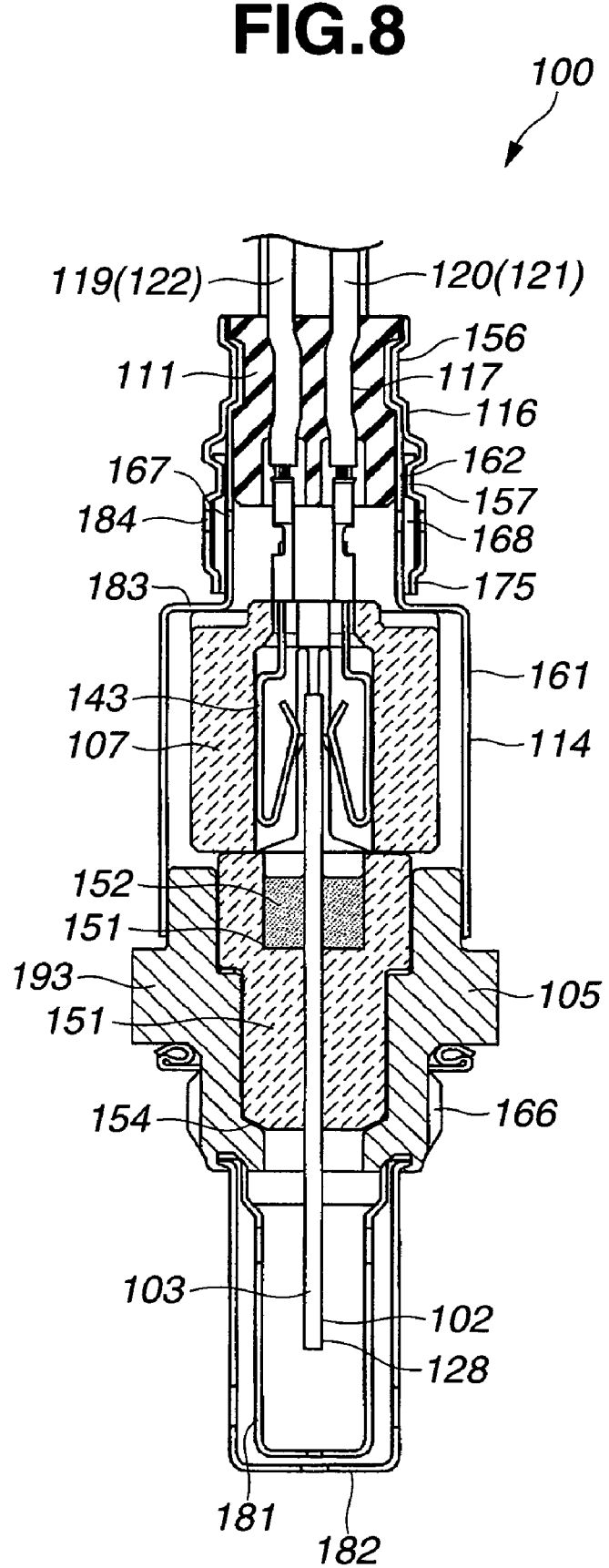
FIG. 8 is a sectional view of a gas sensor according to a second embodiment.

Further, while in the above-described embodiment the crimping section 75 is provided at the place where the outer tubular member 16 and the inner tubular member 14 are directly in contact with each other, this is not for the purpose of limitation but the present invention may be applied to a gas sensor 100 shown in FIG. 8.

The gas sensor 100 according to a second embodiment includes a sensor element 102 in the form of an axially extending plate, a metallic housing 105 holding the sensor element 102 there within, an inner tubular member 114 connected to a rearward end of the metallic housing 105, and an outer tubular member 116 disposed coaxially with the inner tubular member 114 and having disposed there within a rearward side of the inner tubular member 114.

The sensor element 102 includes a detection element 128 for detecting a particular gas component in a measurement gas and a ceramic heater 103, which are formed integral with each other and having a structure known in the art. The metallic housing 105 has a threaded portion 166 for attachment of the gas sensor 100 to an exhaust pipe and a hexagonal portion 193 engaged with an attachment tool at the time of attachment of the gas sensor 100 to the exhaust pipe. With a shoulder portion 154 of the metallic housing 105 is engaged a support member 151 made of alumina. The sensor element 102 is fixed to the support member 151 by a glass seal 152.

Further, to the forward end of the metallic housing 105 are fixed double metallic protectors 181 and 182 covering the forward end portion of the sensor element protruding from the metallic housing 105 and having a plurality of gas inlet holes (no numeral).

Then, the inner tubular member 114 will be described. The inner tubular member 114 is inserted at the forward side thereof into the rearward side of the metallic housing 105. Further, the inner tubular member 114 is formed with, at an axially intermediate portion thereof a shoulder portion 183, at a forward side of the shoulder portion 183 a smaller-diameter portion or forward portion 161 and at a rearward side of the shoulder portion 183 a larger diameter portion or rearward portion 162. The shoulder portion 183 connects between the forward portion 161 and the rearward portion 162. Further, the rearward portion 162 is formed with a plurality of air inlet holes 167 arranged at predetermined circumferential intervals.

Further, at the inside of the forward portion 161 of the inner tubular member 114 is disposed a hollow, nearly cylindrical separator 107. The separator 107 has inserted there into connection terminals 143 (only two are shown in FIG. 8) connected to sensor element lead wires 120, 121 and heater lead wires 119, 122. On the other hand, inside the rearward portion 162 of the inner tubular member 114 is disposed an elastic seal member 111 made of fluororubber having a good heat resistance or the like. This elastic seal member 111 is formed with four lead wire insertion holes 117 extending axially therethrough.

Figure 9:
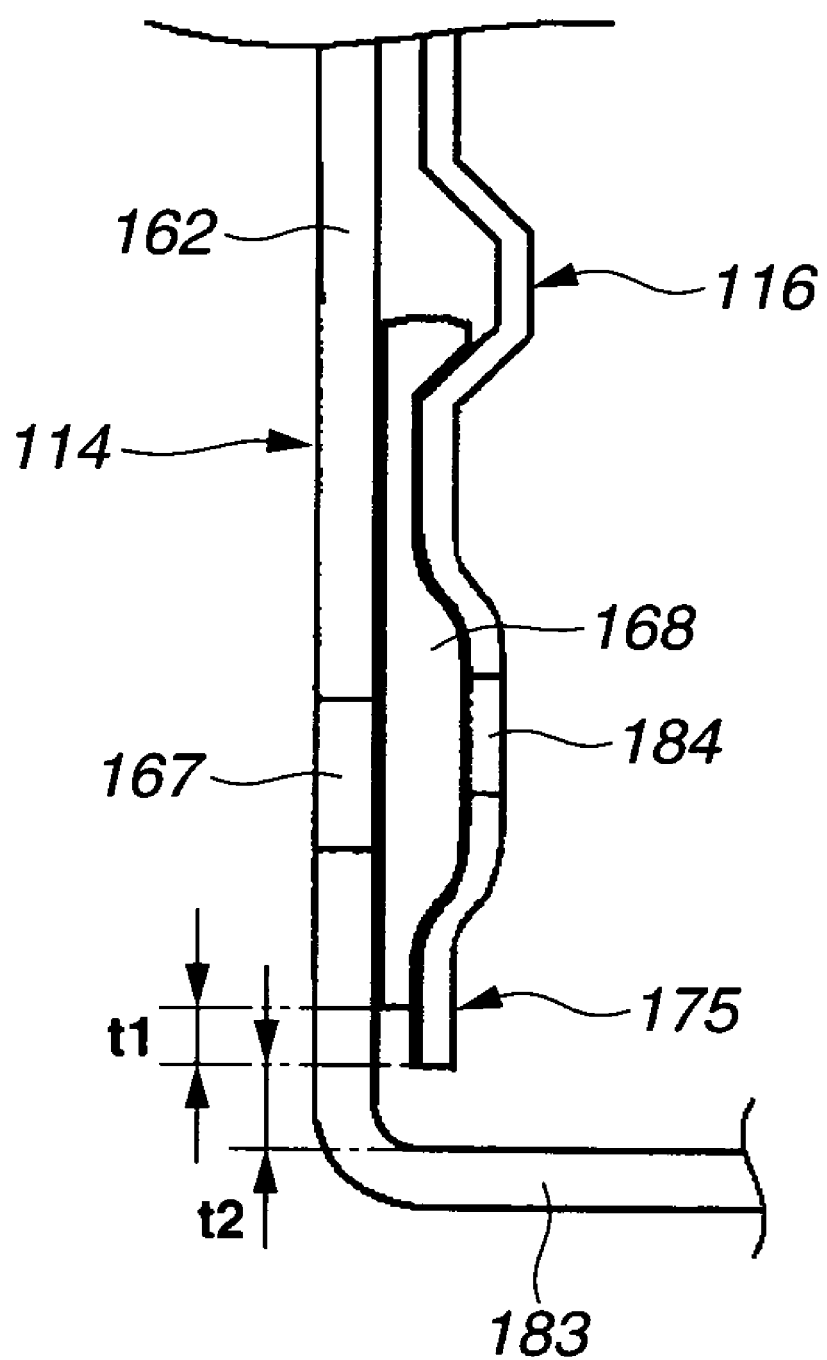
FIG. 9 is an enlarged sectional view of a crimping section and its adjacent portion of an outer tubular member of the gas sensor of FIG. 8.

The outer tubular member 116 is crimped radially inward against the inner tubular member 114. More specifically, as shown in FIG. 9, the outer tubular member 116 has at the rearward side of the filter 168 a crimping section 156 crimped directly against the inner tubular member 114, at the rearward side of the air inlet holes 184 a crimping section 157 crimped against the inner tubular member 114 by way of the filter 168, and at the forward side of the air inlet holes 184 a crimping section 175 crimped against the inner tubular member 114 by way of the filter 168.

The distance between the crimp forward end position that is the position of the forward end of the crimping section 175 and the forward end of the outer tubular member 116 is 1.5 mm or less. By disposing the forward end of the crimping section 175 so as to be axially apart from forward end of the outer tubular member 116 by 1.5 mm or less, a space or gap is not formed between the crimping section 175 and the outer surface of the rearward portion 162 of the inner tubular member 114, so that salt water is not stored at any place and there is not caused any possibility of the inner tubular member 114 and the outer tubular member 116 being corroded. Further, it becomes possible to prevent the fitness in engagement between the crimping section 175 and the rearward portion 162 of the inner tubular member 114 from being lowered.

Further, the axial distance t1 between the forward end of the outer tubular member 116 and the forward end of the filter 168 is set at 0.2 mm. By setting the axial distance t1 between the forward end of the outer tubular member 116 and the forward end of the filter 168 at 0.3 mm or less, the axial length from the forward end of the filter 168 to the forward end of the outer tubular member 116 can be reduced to a desirably small value. Accordingly, the space or gap that is formed at the forward side of the filter 168 and between the forward end of the outer tubular member 116 and the forward end of the inner tubular member 114 can be made smaller, so that it becomes possible to prevent the inner tubular member 114 and the outer tubular member 116 from being corroded by salt water stored therebetween and the detection accuracy of the gas sensor 100 from being lowered.

Further, the axial distance t2 between the shoulder portion 183 of the inner tubular member 114 and the forward end of the outer tubular member 116 is set at 0.6 mm. By setting, in this manner, the axial distance t2 between the inner shoulder portion 183 and the forward end of the outer tubular member 116 at 0.5 mm or more, the axial length from the forward end of the outer tubular member 116 to the shoulder portion 183 can be set at a desirably large value. Accordingly, it becomes possible to prevent salt water from being held between the forward end of the outer tubular member 116 and the shoulder portion 183 by the effect of surface tension for a long period of time. Thus, it becomes possible to prevent the inner tubular member 114 and the outer tubular member 116 from being corroded by stored salt water and the detection accuracy of the sensor from being lowered.

Figure 10:
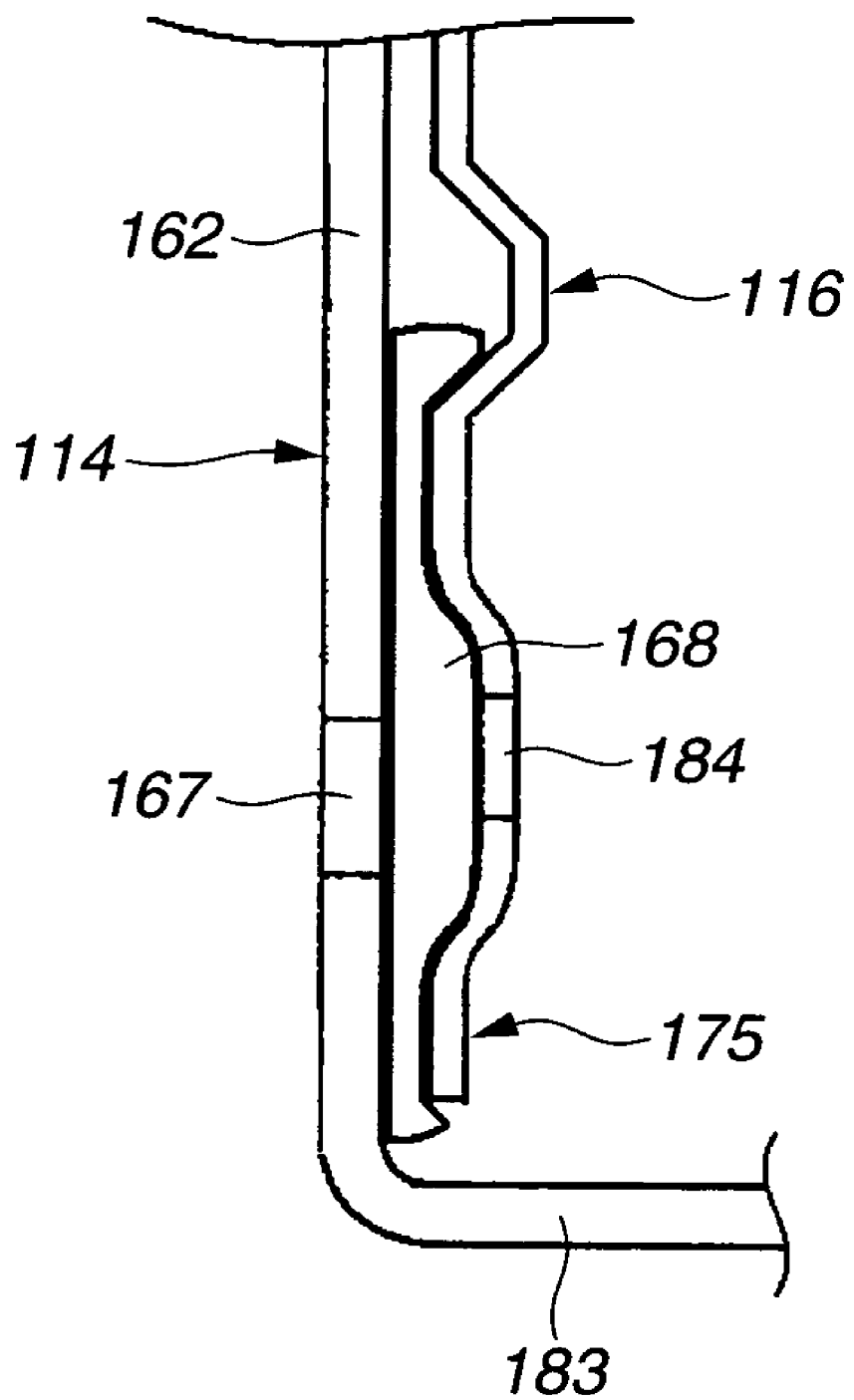
FIG. 10 is an enlarged sectional view of a crimping section and its adjacent portion of a gas sensor according to a variation of the second embodiment.

Further, a sensor according to a variation of the second embodiment is shown in FIG. 10. This variation differs from the embodiment of FIGS. 8 and 9 only in the position of the filter, so that only a different portion is shown in FIG. 10.

Outside the rearward portion 162 of the inner tubular member 114 is disposed a tubular filter 168 for preventing entrance of water through the air inlet holes 167. Further, the outer tubular member 116 is disposed in a way as to cover the peripheries of the filter 168 and the rearward portion 162 of the inner tubular member 114. The outer tubular member 116 is also formed with, at the corresponding position to the filter 168, a plurality of air inlet holes 184 arranged at predetermined circumferential intervals.

The forward end of the filter 168 is disposed more forward than the forward end of the outer tubular member 116. Since the forward end of the filter 168 protrudes from the forward end of the outer tubular member 116, a space or gap between the forward end of the outer tubular member 114 that is disposed more forward than the forward end of the filter 168 can be eliminated, thus making it possible to prevent the inner tubular member 114 and the outer tubular member 116 from being corroded by stored salt water and the detection accuracy of the gas sensor 100 from being deteriorated.

From the foregoing, it will be understood that according to the present invention the forward end of the crimping section is disposed at a distance of 1.5 mm or less from the forward end of the outer tubular member, so that the axial distance between the forward end of the crimping section and the forward end of the outer tubular member can be reduced to a desirably small value. Accordingly, the space or gap between the forward side of the outer tubular member and the forward side of the inner tubular member can be eliminated or smaller, thus making it possible to prevent the inner tubular member and the outer tubular member from being corroded by stored salt water and the detection accuracy of the sensor from being lowered. Further, the spring back phenomenon of the crimping section of the outer tubular member can be reduced. By this, decrease in the surface pressure applied from the crimping section against the inner tubular member can be prevented, thus making it possible to improve the fitness in engagement of the forward end of the crimping section with the outer surface of the inner tubular member. In the meantime, if the axial distance of the forward end of the crimping section from the forward end of the outer tubular member exceeds 1.5 mm, the above-described effect cannot be obtained.

Further, from the point of view of corrosion prevention for the inner tubular member and outer tubular member, it is desirable that the distance between the crimp forward end of the crimping section and the forward end of the outer tubular member is 0 (zero) mm. However, there may possibly occur such a case in which during crimping for forming the crimping section, a crimping tool is moved so as to protrude axially more forward than the forward end of the outer tubular member so that the axial width of the resulting crimping section becomes smaller than desired. Thus, for forming the crimping section of a desired width assuredly, it is preferable that the forward end of the crimping section is disposed axially apart from the forward end of the outer tubular member by a distance of 0.3 mm or more.

It will further be understood that by disposing the forward end of the crimping section so as be axially apart from the forward end of the outer tubular member by a distance of 1.3 mm or less, deterioration of the detection accuracy of the sensor can be prevented further, and the fitness in engagement of the forward end of the crimping section with the outer surface of the inner tubular member can be improved further. Further, by disposing the forward end of the crimping section so as to be axially apart from the forward end of the outer tubular member by a distance of 1.0 mm or less, the detection accuracy of the sensor can be improved more effectively and the fitness in engagement of the forward end of the crimping section with the outer surface of the inner tubular member can be improved more effectively.

It will further be understood that the above-described effects of the present invention can be attained even by the sensor adapted to detect a gas component of a measurement gas by a detection section that is disposed at a forward side thereof.

It will be further understood that according to the present invention, the outer tubular member is thinner than the inner tubular member, so that the spring back phenomenon caused at the crimping section of the outer tubular member can be reduced further. Thus, it becomes possible to further prevent decrease in the surface pressure applied from the crimping section against the outer surface of the inner tubular member and therefore improve the fitness in engagement of the forward end of the crimping section with the outer surface of the inner tubular member. In the meantime, if the outer tubular member is thicker than the inner tubular member, the above-described effect cannot be obtained.

It will be further understood that in case thickness of the outer tubular member is in the range from 0.3 to 0.8 mm, it becomes possible to effectively prevent the surface pressure applied from the crimping section to the inner tubular member from being decreased. In the meantime, if the thickness is less than 0.3 mm, there is a possibility that the strength of the outer tubular member may become less than desired. If the thickness exceeds 0.8 mm, the above-described effect cannot be obtained.

It will be further understood that the Vickers hardness of the outer tubular member at the crimping section is lower than that of the inner tubular member at the crimping section, so that the spring back phenomenon at the crimping section of the outer tubular member can be reduced further. Thus, it becomes possible to prevent decrease in the surface pressure applied from the crimping section against the inner tubular member and improve the fitness in engagement of the forward end of the crimping section with the outer surface of the inner tubular member.

It will be further understood that the outer tubular member is preferably formed of austenite stainless steel. By using austenite stainless steel for the outer tubular member, decrease in the surface pressure applied against the inner tubular member from the crimping section can be prevented more effectively.

It will be further understood that it is preferable to apply the present invention to such a gas sensor in which an inner tubular member and an outer tubular member are formed with one or more air inlet holes for introducing air into the inner tubular member, a filter is disposed at the place corresponding in position to the air inlet holes of the inner tubular member and the outer tubular member, and the crimping section is formed more forward than the filter.

It will be further understood that it is preferable to apply the present invention to such a gas sensor in which an inner tubular member is formed with one or more air inlet holes for introducing air there into, a filter is disposed so as to cover the air inlet holes, and the crimping section is formed so as to interpose the filter between the inner tubular member and the crimping section.

It will be further understood that by disposing the forward end of the inner tubular member and the forward end of the filter so as to be axially apart from each other by a distance of 0.3 mm or less according to the present invention, the axial length from the forward end of the filter to the forward end of the outer tubular member can be reduced to a desirably small value. Accordingly, the space that is formed at the forward side of the filter and between the forward end of the outer tubular member and the forward end of the inner tubular member can be small or can be eliminated, thus making it possible to prevent corrosion of the inner tubular member and the outer tubular member due to salt water stored therebetween and deterioration of the detection accuracy of the sensor. In the meantime, if the axial distance between the forward end of the outer tubular member and the forward end of the filter exceeds 0.3 mm, the above-described effect cannot be obtained.

It will be further understood that by disposing the forward end of the filter more forward than the forward end of the outer tubular member, it becomes possible to prevent a space from being formed between the forward end of the outer tubular member and the outer surface of the inner tubular member, thus making it possible to prevent corrosion of the inner tubular member and the outer tubular member due to salt water stored therebetween and deterioration of the detection accuracy of the sensor.

It will be further understood that by setting, in case the inner tubular member has the shoulder portion between the smaller diameter portion and the larger diameter portion, the axial distance between the forward end of the outer tubular member and the shoulder portion at 0.5 mm or more, the axial length from the forward end of the outer tubular member to the shoulder portion can be made desirably large. Thus, it becomes possible to prevent salt water from being stored between the forward end of the outer tubular member and the shoulder by the effect of the surface tension of salt water for a long period of time. Thus, it become possible to prevent corrosion of the inner tubular member and the outer tubular member due to salt water stored therebetween and deterioration of the detection accuracy of the sensor.

It will be further understood that the present invention is not limited to a gas sensor such as an oxygen sensor but can be applied to various kinds of sensors.

The entire contents of Japanese Patent Applications P2005-364770 (filed Dec. 19, 2005) and P2006-283198 (filed Oct. 18, 2006) are incorporated herein by reference.

Although the invention has been described above by reference to a certain embodiment of the invention, the invention is not limited to the embodiment described above. Modifications and variations of the embodiments described above will occur to those skilled in the art, in light of the above teachings. The scope of the invention is defined with reference to the following claims.

What is claimed is:

1. A sensor comprising:
   a sensor element;
   a metallic housing holding therewithin the sensor element;
   an inner tubular member fixed to an axially rearward end of the metallic housing; and
   an outer tubular member radially surrounding the inner tubular member and having a radially inward crimping section for contact with an outer surface of the inner tubular member,
   wherein an axially forward end of the crimping section is disposed axially apart from an axially forward end of the outer tubular member by a distance of 1.5 mm or less.

2. The sensor according to claim 1, wherein the forward end of the crimping section is disposed axially apart from the forward end of the outer tubular member by a distance of 1.3 mm or less.

3. The sensor according to claim 1, wherein the forward end of the crimping section is disposed axially apart from the forward end of the outer tubular member by a distance of 1.0 mm or less.

4. The sensor according to claim 1, wherein the forward end of the crimping section is disposed axially apart from the forward end of the outer tubular member by a distance of 0.3 mm or more.

5. The sensor according to claim 1, wherein the sensor element is elongated in an axial direction and has at an axially forward side thereof a detection portion at which the sensor element detects a gas component in a measurement gas, the metallic housing surrounds the sensor element in a way as to allow the detection portion to protrude axially forward therefrom, and the inner tubular member surrounds an axially rearward side of the sensor element.

6. The sensor according to claim 1, wherein the outer tubular member is thinner than the inner tubular member.

7. The sensor according to claim 1, wherein the thickness of the outer tubular member is in the range from 0.3 to 0.8 mm.

8. The sensor according to claim 1, wherein the crimping section of the outer tubular member is lower in the Vickers hardness than the inner tubular member.

9. The sensor according to claim 1, wherein the outer tubular member is made of austenite stainless steel.

10. The sensor according to claim 1, wherein each of the inner tubular member and the outer tubular member has one or more of air inlet holes for introducing the air into the inner tubular member, a filter is disposed at a corresponding position to the air inlet holes of the inner tubular member and the outer tubular member, and the crimping section is positioned more axially forward than the filter.

11. The sensor according to claim 1, wherein the inner tubular member has one or more air inlet holes for introducing the air thereinto, and a filter is disposed to cover the air inlet holes, the filter being interposed between the inner tubular member and the crimping section.

12. The sensor according to claim 11, wherein the forward end of the outer tubular member and an axially forward end of the filter are axially apart by a distance of 0.3 mm or less.

13. The sensor according to claim 11, wherein the forward end of the filter is axially more forward than an axially forward end of the outer tubular member.

14. The sensor according to claim 11, wherein the inner tubular member comprises a smaller diameter portion formed with the one or more air inlet holes, a larger diameter portion radially surrounding an axially rearward side of the sensor element and a shoulder portion connecting between the smaller diameter portion and the larger diameter portion, and the forward end of the outer tubular member and the shoulder portion are axially apart by a distance of 0.5 mm or more.

15. The sensor according to claim 1, being adapted for attachment to one of an intake pipe and exhaust pipe of an internal combustion engine.

* * * * *